United States Patent [19]

Nafziger et al.

[11] Patent Number: 4,904,704
[45] Date of Patent: Feb. 27, 1990

[54] RIGID FOAMS PREPARED FROM TREATED TOLUENE DIISOCYANATE RESIDUE

[75] Inventors: John L. Nafziger, Lake Jackson; Steven B. Lowenkron, Houston; Charles E. Koehler, Baytown, all of Tex.; Debkumar Bhattacharjee, Meriden, Conn.

[73] Assignee: The Dow Chemical Company, Midland, Mich.

[21] Appl. No.: 289,082

[22] Filed: Dec. 22, 1988

[51] Int. Cl.$^4$ .............................................. C08G 18/14
[52] U.S. Cl. .................................... 521/156; 521/170; 521/174; 528/73; 528/76; 528/85; 560/330; 560/331; 560/352; 560/353
[58] Field of Search ................ 521/156, 170, 174; 528/73, 76, 85; 560/330, 331, 352, 353

[56] References Cited

U.S. PATENT DOCUMENTS

| | | | |
|---|---|---|---|
| 3,155,699 | 11/1964 | Powers | 260/453 |
| 3,179,680 | 4/1965 | Kober | 260/453 |
| 3,180,852 | 4/1965 | Pfirschke | 260/453 |
| 3,264,336 | 8/1966 | Powers | 260/453 |
| 3,359,295 | 12/1967 | Shultz et al. | 260/453 |
| 3,373,182 | 3/1968 | Powers | 260/453 |
| 3,448,046 | 6/1969 | Schalin | 260/453 |
| 3,450,653 | 6/1969 | McClellan | 260/453 |
| 3,455,836 | 7/1969 | Shultz et al. | 260/453 |
| 3,457,291 | 7/1969 | Baylor | 260/453 |
| 3,458,558 | 7/1969 | Cheng | 260/453 |
| 3,471,417 | 10/1969 | Dickert | 260/2.5 |
| 3,479,384 | 11/1969 | Heiss | 260/453 |
| 3,516,950 | 6/1970 | Haggis | 260/453 |
| 3,573,335 | 3/1971 | Yurimoto et al. | 260/453 |
| 3,634,361 | 1/1972 | Shultz et al. | 260/77.5 |
| 3,646,096 | 2/1972 | Horn | 260/453 |
| 3,723,363 | 3/1973 | Shaw | 260/2.5 |
| 3,755,215 | 8/1973 | Khoury et al. | 250/2.5 |
| 3,759,971 | 9/1973 | Cuscurida et al. | 260/453 |
| 3,793,362 | 2/1974 | Kolakowski et al. | 260/453 |
| 3,799,963 | 3/1974 | Adams | 260/453 |
| 3,887,502 | 6/1975 | Adams | 260/2.5 |
| 3,925,437 | 12/1975 | Rowton | 260/453 |
| 4,032,574 | 6/1977 | Keshi et al. | 260/570 |
| 4,055,585 | 10/1977 | Okamoto et al. | 260/453 |
| 4,143,008 | 3/1979 | Zwolinski et al. | 260/18 |
| 4,251,401 | 2/1981 | Reischl | 260/9 |
| 4,251,638 | 2/1981 | Reischl | 521/128 |
| 4,293,456 | 10/1981 | Reischl | 260/9 |
| 4,297,456 | 10/1981 | Reischl | 525/452 |
| 4,489,177 | 12/1984 | O'Connor et al. | 260/453 |
| 4,595,709 | 6/1986 | Reischl | 521/79 |
| 4,654,443 | 3/1987 | Marks et al. | 564/305 |

FOREIGN PATENT DOCUMENTS 238988 10/1986 German Democratic Rep. .

Primary Examiner—Maurice J. Welsh
Attorney, Agent, or Firm—Carol J. Cavender

[57] ABSTRACT

A method of treating toluene diisocyanate distillation residues comprising reacting the residues with at least about 0.5 equivalents, based on hydrolyzable chloride concentration of the residues, of an epoxy compound at a temperature of from about 155 to about 220° C. to produce a treated distillation residue having a hydrolyzable chloride level of less than about 800 parts per million (ppm) is taught. The product of the method is useful, for instance, in producing rigid foams with low K Factors.

46 Claims, No Drawings

RIGID FOAMS PREPARED FROM TREATED TOLUENE DIISOCYANATE RESIDUE

BACKGROUND OF THE INVENTION

This invention relates to the treatment of distillation residues from the preparation of toluene diisocyanate. More particularly the invention relates to such treatment to form products useful in the production of rigid foams.

It is known to prepare toluene diisocyanates by the phosgenation of toluene diamine. Typical processes for the phosgenation of amines may be found in U.S. Pat. Nos. 2,680,127; 2,822,373 and 3,781,320. In the phosgenation of toluene amines to form toluene diisocyanates, the product diisocyanate is generally distilled from the reaction mixture in which it is prepared. At the conclusion of the distillation, the reaction mixture normally contains a quantity of high boiling residue. Such residue generally comprises polymeric materials such as alpha, omega-isocyanatobiurets, polycarbodiimides, diisocyanato-carbodiimides, polyuretidinediones, isocyanurates and various other isocyanate adducts. Since this residue is seldom commercially useful, it it usually disposed of.

A number of processes for use of distillation residues have been developed, primarily for methylene diphenylisocyanate. Some of the processes involve reduction of acidity levels. There are many procedures known for treating organic isocyanates to reduce acidity levels. For example, U.S. Pat. No. 3,264,336 discloses a fractional distillation. U.S. Pat. No. 3,516,950 discloses a volatilization of hydrogen chloride. Other methods have been described that include treatment of organic isocyanates with certain metals, e.g., iron, copper, zinc, aluminum, nickel, cobalt and the like, organic complexes of such metals and halides salts of such metals. Such treatments generally involve separation of a reaction product from the isocyanate residue by distillation or other procedure employing heat. See U.S. Pat. Nos. 3,155,699; 3,264,336; 3,373,182 and 3,458,558. The heat is often sufficient to increase viscosity of the isocyanate residue.

A method of chloride hydrolysis for reduction of hydrolyzable chloride in isocyanates is described in U.S. Pat. No. 3,179,680. Acidity can be reduced concurrently with chloride removal by volatilization of hydrogen chloride present. (See U.S. Pat. No. 3,516,950). Epoxide compounds have been employed in reaction processes as acid acceptors (see for example U.S. Pat. No. 3,448,046). Certain epoxide compounds have also been suggested for use in reducing acidity and hydrolyzable chlorides in certain isocyanate compounds, as disclosed in U.S. Pat. Nos. 3,793,362; 3,925,437 and East German Patent 238,988 to Baum et al. The products of processes taught in the first two references are specific to polymethylene polyphenylisocyanates. The products of processes taught in Baum reference are often unsatisfactory for producing useful polyurethane foams.

Certain toluene diisocyanate residues have been mixed with certain amounts of methylene bis(phenylisocyanate) according to processes described in U.S. Pat. Nos. 3,634,361 and 3,455,836. Several uses of such mixtures are suggested including making certain polyurethanes. These too, have limited utility. Distillation residues of toluene diisocyanate have not generally proven useful in forming foams having good insulative qualities.

Rigid foams are useful in a variety of applications including insulative foams, flotation devices, furniture, decorative materials, high density structural foams and the like. Insulative rigid foams are used, for instance, to insulate vessels; pipelines; ice chests; appliances such as refrigerators; buildings and the like. Laminates of such insulative foams are used in roofing, sheathing and the like.

For use in insulation, a foam is advantageously a poor thermal conductor. Thermal conduction is measured by the K factor as described in ASTM C 177-85 and C-518-76. The lower the value of its K factor, the better insulator a material is.

It is, therefore, desirable to treat toluene diisocyanate distillation residues such that they are useful in making products such as rigid foams. Desirably, such foams have lower K factors than other, similar foams.

SUMMARY OF THE INVENTION

In one aspect, the invention is a method of treating toluene diisocyanate distillation residues comprising reacting the residues with at least about 0.5 equivalents per equivalent of hydrolyzable chloride in the residue, of an epoxy compound at a temperature of from about 155° C. to about 220° C. to produce a treated distillation residue having a hydrolyzable chloride concentration of less than about 800 parts per million (ppm).

In another aspect, the invention is a treated toluene diisocyanate distillation residue which is the product of reacting the residue with an epoxy compound at a temperature of from about 155° C. to about 220° C., said treated toluene diisocyanate distillation residue having a hydrolyzable chloride concentration of less than about 800 parts per million (ppm).

In another aspect, the invention is a polymer prepared by reacting a reaction mixture containing components:
(a) an active hydrogen compound or mixture thereof; and
(b) a polyisocyanate component containing
  (1) from about 1 to about 100 weight percent based on total weight of polyisocyanate component (b) of a treated toluene diisocyanate distillation residue which is the product of reacting the residue with an epoxy compound at a temperature of from about 155° C. to about 220° C., said treated toluene diisocyanate distillation residue having a hydrolyzable chloride level of less than about 800 parts per million (ppm).

In yet another aspect, the invention is a process for preparing a polymer by reacting a reaction mixture containing components:
(a) an active hydrogen compound or mixture thereof; and
(b) a polyisocyanate component containing
  (1) from about 1 to about 100 weight percent based on total weight of polyisocyanate component (b) of a treated toluene diisocyanate distillation residue which is the product of reacting the residue with an epoxy compound at a temperature of from about 155° C. to about 220° C., said treated toluene diisocyanate distillation residue having a hydrolyzable chloride level of less than about 800 parts per million (ppm).

The polymers prepared by the process of the invention are suitably in any form, but are particularly useful as foams which are advantageously isocyanurate foams or polyurethane foams, including polyurethane-polyurea foams. Insulative foams prepared according to the practice of the invention have particularly desirable K-factors.

DETAILED DESCRIPTION OF THE INVENTION

Distillation residue from the distillation of any toluene diisocyanate is suitably used in accordance with the present invention. The distillation residue employed herein is advantageously formed in the phosgenation of toluene diamine to form a toluene diisocyanate. After phosgenation, the product diisocyanate is removed from the reaction mixture by distillation. The distillation residue is that portion of the reaction mixture which remains following the removal of product diisocyanate. However, the distillation residue employed herein preferably contains a quantity of the diisocyanate such that the distillation residue is generally a liquid at the temperatures as which it is produced, and more preferably also liquid at the temperatures of treatment. The distillation residues referred to herein advantageously contain from about 13 to about 35, preferably from about 20 to about 30 weight percent free toluene diisocyanate. The distillation residues generally have an isocyanate group (NCO) content from 22 to about 45, preferably from about 30 to about 40 percent by weight and are substantially free of solvent.

If the distillation residue is released from a still immediately after distilling the toluene diisocyanate, it is generally a black tarry liquid, but when a residue which is less than about 20 weight percent toluene diisocyanate is allowed to cool to about 35° C., the residue solidifies to a pitch-like solid which breaks but flows over time. Such cooling delays irreversible hardening such as that observed within about 6 hours at about 150°–250° C. Because the hardening occurs even at low temperatures, delays between production of the residue and its treatment are preferably avoided.

The chemical composition of the residues is not certain, but the residue generally comprises mixtures of materials such as polyureas, (poly)biurets, alpha, omega-isocyanato-biurets, polycarbodiimides, polyuretdiones, isocyanurates, diisocyanatocarbodiimides, addition products of monomeric diisocyanates and carbodiimides, isocyanurates, polyisocyanates that have polyuretidinedione groups and the like. Such materials usually contain free or capped isocyanate groups.

The distillation residues generally contain residual acidic materials. The term "acid", is used herein to refer to these contaminates and refers to free hydrogen chloride and/or labile covalently bonded chloride present in the isocyanate, such as carbamoyl chlorides and other various types of materials present in the isocyanate compounds that respond as acids in standard analytical tests.

The acid content or level is readily determined by standard analytical tests such as ASTM D-1638, the procedure described in U.S. Pat. No. 3,793,362 (which is incorporated by reference herein in its entirety) or other tests for acidity. These tests generally comprise heating the isocyanate in a solution of mixed alcohols or toluene and methanol, and titrating the resulting mixture with dilute potassium hydroxide. The acidity is expressed as weight percent hydrochloric acid, whatever the acid-producing components actually are.

The term "hydrolyzable chloride" refers to labile chloride atoms which are free, ionically bonded or covalently bonded within a compound, but have more ionic character than, for example, the chlorine atom present in chlorobenzene. The hydrolyzable chloride value is also referred to as chloride equivalent, chloride level and chloride concentration. Hydrolyzable chloride is determined by extracting the chloride from the isocyanate contaminants by hydrolysis or alcholysis such as in a mixed alcohol solvent media and titration of the resulting chloride ion concentration such as with silver nitrate. Conveniently, an admixture of a known weight of toluene diisocyanate distillation residue and mixed alcohols which boil between 70° and 75° C., in a quantity sufficient to react with the diisocyanate and dissolve the products of the reaction therewith is prepared. Any mixture of alcohols which boils in that range and reacts the residue to dissolve it is suitable. Conveniently, the mixture is a mixture of an alkanol such as methanol and an alkanolether such as methoxyethanol or methoxypropanol and the like. A solution is formed by stirring and heating the admixture sufficiently to form a solution and, advantageously, heated to 70°–75° C., for a time sufficient to release the desired chlorides to solution, preferably, for the practice of this invention, 7.0 minutes. The solution is, then, removed from heat and a quantity of concentrated (85 weight percent) nitric acid sufficient to maintain activity of silver/silver chloride electrodes used to determine the end point of titration is added. The quantity of nitric acid is conveniently about 0.5 to 1 weight percent of the total solution. After the solution cools for about 5 minutes, the electrodes are inserted and titration with a dilute solution (e.g. 0.05 Normal (N)) solution of silver nitrate is begun. Titration is ended when a 280 millivolt (mv) inflection point is reached. The concentration of hydrolyzable chloride is calculated from the amount of silver nitrate required. Determination of chloride is exemplified in Example 1 hereinafter and corresponds to the procedure of ASTM D-1638 with titration of chloride by silver nitrate rather than acidity by hydroxide and using the 7.0 minute heating before titration.

The hydrolyzable chloride concentration of a treated toluene diisocyanate residue is advantageously reduced to less than about 800 parts per million (ppm), preferably less than about 600 ppm, most preferably less than about 400 ppm, even more preferably less than about 300 ppm, advantageously by treatment with an epoxy compound. Hydrolyzable chloride levels of less than about 400 ppm are particularly advantageous when the treated distillation residue is to be used to make a foam without the use of other isocyanate compounds. Toluene diisocyanate distillation residues treated with epoxy compounds are referred to herein as "treated distillation residues." Diluents are, optionally, present therein.

Suitable epoxy compounds include monoepoxy compounds including alkylene oxides such as butylene oxide (all isomers), propylene oxide, ethylene oxide, styrene oxide and the like, as well as glycidyl ethers such as cresyl glycidyl ethers, phenylglycidyl ether and the like; epoxy resins, including those formed from epichlorohydrin and bisphenols, such as bisphenol A and bisphenol F and the like, as well as aliphatic and cycloaliphatic epoxy resin such as epoxy cyclohexyl methyl, epoxy cyclohexyl carboxylates; cresol resins Novalac resins and the like. Epoxy compounds having more than one epoxy group preferably have molecular weights of from about 100 to about 1000. Preferred epoxy compounds include the epoxy resins and monoepoxy compounds. More preferred epoxy compounds are monoepoxy compounds having molecular weights of from about 44 to about 1000 because lower viscosities are, advantageously, attained using such monoepoxy compounds. It is, however, more preferable, in many instances, to use epoxy compounds which boil at temperatures above those used in the treatment to avoid the need for high pressure equipment to contain vapors.

The epoxy compounds are suitably used in amounts of at least about 0.5, preferably from about 0.5 to about 20 epoxy equivalents per equivalent of chloride, more preferably, in amounts of from about 0.75 to about 3; most preferably from about 1 to about 3 epoxy equivalents per equivalent of chloride. When more than about 3 epoxy equivalents are used, viscosity increases are generally noted. The term "epoxy equivalent" as used herein means that amount of epoxide compound which contains an average of one epoxy group.

In the case of batch processes, it is generally preferable to add the epoxy compound to the distillation residues such that local concentrations of epoxide remain low. The epoxy compound is, therefore, preferably, added slowly, for instance, over a period of from about 10 minutes to an hour, more preferably from about 20 to about 40 minutes for batches of residue weighing greater than a kilogram. Continuous addition is suitable for a continuous process, but the continuous addition is preferably slow addition. A thorough and uniform blending of the epoxide compound into the toluene diisocyanate distillation residue is desirable. This is suitably accomplished, for instance, by vigorous stirring of the toluene diisocyanate distillation residue while gradually adding the epoxide compounds, and continuing agitation of the mixture at least about 2 minutes, preferably from about 5 to about 15 minutes after addition is complete.

According to the present invention, the epoxy compound and the toluene diisocyanate distillation residue are admixed by the utilization of any liquid mixing device. The mixing can be carried out batchwise or continuously in accordance with procedures within the skill in the art. Advantageously, in the described process, the epoxy compound is easily blended readily and intimately with toluene diisocyanate distillation residue.

It has been found that a more reactive product, especially useful in forming foams of low K factor, is formed when the epoxy compound and the distillation residue are mixed or reacted at a temperature of at least about 155° C. The temperature is advantageously kept below about 220° C. to avoid undesirable viscosity increases. A preferred temperature range is from about 165° C. to about 210° C. more preferably from about 165° C. to about 180° C. Such heating is preferably maintained at least about 10 minutes, preferably at least about 30 minutes and, most preferably, sufficiently long to allow reaction of the chlorides and epoxy compounds to approach completion. While chloride level may be further lowered by allowing the mixture to stand at ambient temperature (about 32°–37° C.) for periods of several hours, such standing, generally results in viscosity increase. In most cases, sufficiently low chloride concentrations are reached within less than about 2 hours, preferably less than about one hour, after the heat is removed. In the usual case, when a lower viscosity is desirable, the treated distillation residue is diluted or used without storage or standing, especially at temperatures over about 150° C., to avoid viscosity increase.

When storage is necessary, the treated residue is preferably cooled to less than about 115° C., preferably from about 50° C. to about 115° C.

The mixing operations are preferably carried out in the absence of moisture inasmuch as isocyanates are known to be susceptible to reaction with moisture. Any known procedure for admixing liquids in a dry atmosphere may be employed. Some examples of conventional techniques include the utilization of an inert gas atmosphere, such as nitrogen, the control of humidity in an atmosphere, and the like.

The treated distillation residues formed by treatment with epoxy compounds as described in the preferred temperature range are of novel composition, different from distillation residues treated by processes known in the art. That composition difference is evident from the fact that distillation residues treated by the process of the invention can be used to produce, for instance, rigid isocyanurate foams having excellent insulation properties as described hereinafter, which foams are not produced from previously known treated distillation residues. Treated distillation residues of having the novel composition suitable for making the foams are also recognizable by their low chloride concentrations as discussed previously.

While the treated toluene diisocyanate distillation residue is suitably used without dilution, for instance to prepare a foam, advantageously, the treated isocyanate is blended with a polyisocyanate different from the treated distillation residue in an amount sufficient to lower the viscosity to a preselected viscosity or to achieve a desired reactivity as evidenced by foam formation and the qualities of the foam formed. It is not critical when the polyisocyanate is added to a toluene diisocyanate residue; before, during or after treatment is suitable. Treatment before dilution is, generally preferred for convenience in handling and heating as well as avoidance of reacting even more dilute chemical species. Some dilution before treatment is advantageous, however, in situations where the residue is inconveniently viscous. The polyisocyanate used for dilution is suitably any, preferably liquid, organic isocyanate compound having an average of more than one isocyanate group per molecule. The polyisocyanate is suitably crude or distilled, but preferably has a viscosity less than that of the treated toluene diisocyanate distillation residue. Such polyisocyanate compounds are well known and readily available commercially.

Exemplary suitable polyisocyanates include aromatic, aliphatic and cycloaliphatic polyisocyanates and combinations thereof. Representative polyisocyanates includes diisocyanates such as m-phenylene diisocyanate, toluene-2,4-diisocyanate, toluene-2,6-diisocyanate, hexamethylene-diisocyanate, tetramethylene-diisocyanate, cyclohexane-1,4-diisocyanate, hexahydrotoluene diisocyanate (and isomers thereof), 1-methoxyphenyl-2,4-diisocyanate, diphenylmethane-4,4'-diisocyanate, diphenylmethane-2,4'-diisocyanate, 3,3'-dimethyl-4,4'-biphenyl diisocyanate, 3,3'-dimethyldiphenyl-methane-4,4'-diisocyanate and the like; triisocyanates such as 4,4',4''-triphenylmethane triisocyanate, toluene-2,4,6-triisocyanate, and the like; tetraisocyanates such as 4,4'-dimethyldiphenyl-methane-2,2',5,5'-tetraisocyanate, 4,4'-dicyclohexane-diisocyanate, isophorone diisocyanate, isomers of each and the like; as well as other polyisocyanates such as polyphenylisocyanate and the like and mixtures thereof. Toluene diisocyanate, diphenylmethane-4,4'-diisocyanate, diphenylmethane- 2,4'-diisocyanate and polymethylene polyphenylisocyanate are beneficial for use in the practice of the invention because of their availability and properties. Mixtures of polyisocyanate components are suitably used in the practice of the invention.

Polymethylene polyphenylisocyanates, or polymeric methylene diphenylisocyanates (PMDI), are more preferred for use in the practice of the invention. Polymethylene polyphenylisocyanates are mixtures containing from about 35 to about 85, preferably from about 65 to about 75 percent by weight of methylenebis (phenylisocyanate), the remainder of the mixture being comprised of closely related polyisocyanates of higher molecular weight and functionality greater than about two. They are well known compositions, and are commercially prepared by phosgenation of mixtures of the corresponding methylene-bridged polyphenyl polyamines. The latter, in turn, are obtained by interaction of formaldehyde, hydrochloric acid and primary aromatic amines such as aniline, o-chloroaniline, o-toluidine, and the like using procedures well known in the art. Illustrative of known methods for preparing methylene-bridged polyphenyl polyamines and polymethylene polyphenylisocyanates therefrom are those described in U.S. Pat. Nos. 2,683,730; 2,950,263; 3,012,008; 3,344,162 and 3,362,979; Canadian Pat. No. 700,026 and German specification 1,131,877. Polyisocyanates suitable for use in the practice of the invention include those available commercially from The Dow Chemical Company under the trade designation PAPI ®.

Blends of the invention comprise from about 1 to about 100 percent by weight treated toluene diisocyanate residue and from about 99 to about 0 weight percent diluent polyisocyanate. From about 90 to about 100 weight percent treated residue based on total weight of a blend is suitably used; however, preferably the treated residue blend contains at least about 10, more preferably from about 15 to about 75, most preferably from about 20 to about 40 weight percent treated residues based on total weight of the blend. The relative proportions of residue and polyisocyanate are generally selected to achieve a preselected viscosity and preselected properties in resulting products. Advantageously, the relative proportions of treated residue and polyisocyanate are selected to achieve a viscosity suitable for a use of the blend. A larger proportion of treated distillation residue can be used with less viscous polyisocyanates like toluene diisocyanate (TDI) than with more viscous polyisocyanates like methylene diphenylene isocyanate (MDI) and derivatives thereof. Advantageously for use in making foams, the blend has a viscosity of less than about 10,000 cps (centipoise), preferably from about 30 to about 3000, more preferably from about 40 to about 2500 cps. When a blend is to be used for a specific application, the viscosity is most preferably preselected for convenience in preparing that type of foam by processes known to those skilled in the art. For instance, in the case of insulative polyurethane foams, viscosity is generally preferably from about 200 to about 3000. Also, when residues are to be used in applications sensitive to such levels of chloride, and more than about 400 ppm of hydrolyzable chlorides are present in the treated distillation residues, the residues are preferably blended with isocyanates having less hydrolyzable chloride such that the blend has less than about 400 ppm, preferably less than about 300 ppm, of hydrolyzable chlorides.

When polymethylene polyphenylisocyanates are blended with the treated toluene diisocyanate residues, blends are preferably at least as reactive as the starting polymethylene polyphenylisocyanates. This reactivity is measured by the times from mixing of isocyanate with active hydrogen compounds until specific phenomenon are observed in a forming polyurethane or polyisocyanurate foam. These measures of reactivity include cream time, visual rise time, gel time, and tack-free time.

Blends of the treated distillation residues and liquid polyisocyanates are suitably used to make polyisocyanurate, polyurethane, polyurethane-polyureas polymers and the like. The polymers suitably take the form of products such as flexible or rigid foams, adhesives, binders and the like. Rigid polyisocyanurate and polyurethane foams prepared using the blends of the invention are particularly useful because of their low K factors. Polyisocyanurate foams (or isocyanurate foams) are foams formed using a ratio of isocyanate groups to active hydrogen groups of at least about 1.3, preferably, in the presence of trimerization catalysts as discussed hereinafter. Polyurethane foams are formed when little trimerization of isocyanate takes place, and polymer formation is primarily the reaction of active hydrogen groups of an active hydrogen component with isocyanate groups of a polyiocyanate component.

Rigid foams are foams which rupture when a 200×25×25 mm sample is bent around a 25 mm mandrel at a uniform rate of one lap in 5 sec at a temperature between 18 and 29C, according to ASTM 1566-82. Flexible foams do not rupture under these conditions. Advantageously, a rigid foam has a tensile strength to compressive strength ratio of about 1:0.5.

Any suitable organic compound containing at least two active hydrogen containing groups as determined by the Zerewitinoff method may be used for reaction with the treated distillation residues or blends thereof with other polyisocyanates. Active hydrogen compounds are compounds having hydrogen-containing functional groups which will react with an isocyanate group. The Zerewitinoff test described by Kohler in the *Journal of the American Chemical Society*, Vol. 49, page 3181 (1927) predicts the tendency of a hydrogen-containing group to react with isocyanates. Suitable active hydrogen compounds are those conventionally employed in the preparation of polyurethanes such as the compounds described in U.S. Pat. No. 4,394,491, particularly in columns 3 through 5 thereof, wherein the compounds are called polyahls, which patent is incorporated herein by reference in its entirety. Suitable active hydrogen compounds are generally liquids or solids capable of being melted at relatively low temperatures.

Active hydrogen components most commonly used in polyurethane production are those compounds having at least two hydroxyl groups, which compounds are referred to as polyols. Representatives of suitable polyols are generally known and are described in such publications as *High Polymers*, Vol. XVI, "Polyurethanes, Chemistry and Technology" by Saunders and Frisch, Interscience Publishers, New York, Vol. I, pp. 32–42, 44–54 (1962) and Vol. II pp 5–6, 198–199 (1964); *Kunststoff-Handbuch*, vol. VII, Vieweg-Hochtlen, Carl-Hanser-Verlag, Munich, pp. 45–71 (1966); and *Organic Polymer Chemistry* by K. J. Saunders, Chapman and Hall, London, pp. 323–325 (1973); and *Developments in*

*Polyurethanes,* Vol. 1, J. M. Burst, ed., Applied Science Publishers (1978) pp. 1–76.

Typical polyols include polyester polyols, polyester amide polyols, and polyether polyols having at least two hydroxyl groups. Polyethers and polyesters having hydroxyl terminated chains are preferred for use as relatively high molecular weight active hydrogen containing compounds for use in polyurethanes suitable for use in the practice of the invention. Examples of polyols also include hydroxy functional acrylic polymers, hydroxyl-containing epoxy resins, polyhydroxy terminated polyurethane polymers, polyhydroxyl-containing phosphorus compounds and alkylene oxide adducts of polyhydric thioethers, including polythioethers, acetals, including polyacetals.

Polyether polyols advantageously employed in the practice of this invention are polyalkylene polyether polyols including the polymerization products of oxiranes or other oxygen-containing heterocyclic compounds such as tetramethylene oxide in the presence of such catalysts as boron trifluoride potassium hydroxide, triethylamine, tributyl amine and the like, or initiated by water, polyhydric alcohols having from about two to about eight hydroxyl groups, amines and the like. Illustrative alcohols suitable for initiating formation of a polyalkylene polyether include ethylene glycol, 1,3-propylene glycol, 1,2-propylene glycol, 1,4-butylene glycol, 1,3-butylene glycol, 1,2-butylene glycol, 1,5-pentane diol, 1,7-heptane diol, glycerol, 1,1,1-trimethylolpropane, 1,1,1-trimethylolethane, hexane-1,2,6-triol, alpha-methyl glucoside, pentaerythritol, erythritol, pentatols and hexatols. Sugars such as glucose, sucrose, fructose, maltose and the like as well as compounds derived from phenols such as (4,4'-hydroxyphenyl)2,2-propane, and the like are also suitable polyhydric alcohols for forming polyether polyols useful in the practice of the invention.

The treated distillation residues of the invention are advantageously reacted with active hydrogen compounds in the presence of blowing agents. Any blowing agent or mixture thereof is suitable for use in the practice of the invention. Suitable blowing agents include inorganic blowing agents such as water, organic blowing agents which are volatile at temperatures in the mold, and dissolved inert gases. Suitable organic blowing agents include acetone; ethyl acetate; methanol; ethanol; halogen substituted alkanes such as methylene chloride, chloroform, ethylidene chloride, vinylidene chloride, monofluorotrichloromethane, chlorodifluoromethane, dichlorodifluoromethane and the like; butane; hexane; heptane; diethyl ether; and the like. Gases inert to the starting components such as nitrogen, air, carbon dioxide and the like are also useful blowing agents. Compounds such as azides which decompose at temperatures present in the mold to produce gases such as nitrogen are also useful. Preferred blowing agents are compounds which boil between about $-50°$ and $100°$ C., more preferably between about $0°$ and $50°$ C.

The amount of such blowing agent employed is not critical to the invention, but should be sufficient to foam the reaction mixture. Said amount will vary with factors such as the density desired in a foamed product.

Water is another useful blowing agent for use in the practice of the invention. In addition to generating gas for foaming, water reacts quickly with polyisocyanate components, thus contributing to early polymer strength needed for gas retention. Generally, when water is used, it is present in proportions of from about 1.5 to about 8 weight percent of water based on total weight of active hydrogen components. Other blowing agents, such as those previously discussed, can be used with water.

Rigid polyisocyanurate and polyurethane foams prepared from the treated distillation residue of the invention are particularly useful. Those skilled in the art of preparing such foams can readily use the treated TDI distillation bottoms of the invention or blends thereof with other polyisocyanates to prepare the foams.

Any method is suitably used to prepare a rigid polyisocyanurate foam using the treated toluene diisocyanate residues or blends thereof with other polyisocyanates. For instance, the process of U.S. Pat. No. 4,604,410, which is incorporated herein by reference in its entirety, is followed substituting the treated distillation residues or blends of the invention for other polyisocyanates. Preferably, the treated distillation residues or blends of the invention are reacted with a polyfunctional active hydrogen compound in the presence of a catalyst which catalyzes the formation of isocyanurates and a blowing agent suitable for forming foams having preselected physical properties.

Suitable catalysts are any which catalyze the formation of isocyanurates such as those mentioned in *High Polymers,* Vol. XVI, "Polyurethanes, Chemistry and Technology" by Saunders and Frisch, Interscience Publishers, New York, part 1, pp. 94–97 (1962). Such catalysts are referred to herein as trimerization catalysts. Exemplary of these catalysts include aliphatic and aromatic tertiary amine compounds, organo-metallic compounds, alkali metal salts of carboxylic acids, phenols and symmetrical triazine derivatives. Preferred catalysts include potassium salts of carboxylic acids such as potassium octoate and tertiary amines such as, for instance, 2,4,6-tris(dimethyl aminomethyl) phenol.

Preferred active hydrogen compounds for use in preparing rigid isocyanurate foams are those having equivalent weights less than about 240, more preferably less than about 200. Among those active hydrogen compounds, polyester polyols, such as those prepared from terephthalic acid and polyalkylene glycols such as polyethylene glycols are generally preferred over the polyether polyols. The treated distillation residues alone or in blends with additional polyisocyanate(s) are advantageously reacted with the polyfunctional active hydrogen compounds in a ratio of from about 1.3 to about 6, preferably about 2 to about 4 equivalents of isocyanate to active hydrogen groups to form foams high in isocyanurate groups.

In the preparation of isocyanurate foams, the blowing agent is most preferably at least partially a hydrocarbon or halohydrocarbon. The blowing agent is advantageously used in an amount sufficient to achieve a preselected density between about 0.4 and 20 pounds per cubic foot (pcf), preferably from about 1 to about 5 pcf. Such densities are advantageously achieved using from about 1 to about 30 percent by weight blowing agent based on total formulation weight (including all active hydrogen compounds, polyisocyanates and additives).

Advantageously, rigid polyisocyanurate foams of the invention have K factors at least about 0.003 British Thermal Units inch/hour-square foot °F. (BTU in/hr ft$^2$ °F.), ($4.3 \times 10^{-4}$ watt/meter °K. (w/mK)) preferably at least about 3%, more preferably at least about 5% lower than corresponding foams manufactured from polymethylene polyphenylisocyanates of the same viscosities, with the same active hydrogen compounds, blowing agents, catalysts, surfactants and other additives. More preferably, the foams of the invention have K factors (mean temperature at 75° F.) of less than about 0.115, preferably less than about 0.112, more preferably from about 0.102 to about 0.112 (BTU in/hr ft$^2$ °F.) (less than about 0.0166, less than about 0.0161, from about 0.0147 to about 0.0161 Watt per meter Kelvin (w/m K), respectively). Rigid isocyanurate foams of the invention also advantageously have less tendency to crumble as determine by the friability test described in ASTM C-421-77 than have foams prepared from polymeric methylene diphenylisocyanate of the same viscosity and the same other ingredients as the foam of the invention. The percent friability of foams of the invention is advantageously less than about 60%, preferably less than about 50%, more preferably less than about 40% of that of a corresponding foam prepared polymeric methylene diphenylisocyanate.

Any effective method is suitably used to prepare a polyurethane foam. The treated TDI distillation residues or blends thereof of the invention are substituted for other polyisocyanates. Preferably, the treated distillation residues or blends of the invention are reacted with an polyfunctional active hydrogen compound in the presence of a catalyst which catalyzes the formation of polyurethane bonds and a blowing agent suitable for forming foams having preselected physical properties.

One or more catalysts are beneficially used in making polyurethanes. Suitable catalysts for preparation of polyurethane foams are any which catalyze reactions of isocyanates with active hydrogen groups such as hydroxyl groups or catalyze the reaction between water and an isocyanate such as those mentioned in *High Polymers*, Vol. XVI, "Polyurethanes, Chemistry and Technology" by Saunders and Frisch, Interscience Publishers, New York, part 1, pp. 211–215 (1962). Such catalysts are referred to herein as polyurethane catalysts. Suitable catalysts include tertiary amines, such as, triethylenediamine, N-methyl morpholine, N-ethyl morpholine, diethyl ethanolamine, 1-methyl-4-dimethylaminoethyl piperazine, 3-ethoxy-N-dimethylpropylamine, N,N-dimethyl-N',N'-methyl isopropyl propylene diamine, N,N-diethyl-3-diethylaminopropylamine, dimethyl benzylamine, triethylamine, tributylamine, bis(N,N-diethylaminoethyl)adipate, 2-methylimidazole, 1,4-diaza-bicyclo(2,2,2)-octane and the like. Other suitable catalysts include tin compounds such as stannous chloride, tin salts of carboxylic acids such as dibutyltin di-2-ethyl hexoate, dibutyl tin dilaurate, dibutyltin diacetate, di-2-ethylhexyltin oxide, stannous octoate and the like, as well as other organometallic compounds such as compounds of iron, lead, arsenic, antimony, mercury and bismuth and compounds disclosed in U.S. Pat No. 2,846,408 and the like. Silamines having carbon-silicon bonds such as those described in German Pat. No. 1,229,290 including 2,2,4-trimethyl-2-silamorpholine and the like as well as basic nitrogen compounds such as tetraalkylammonium hydroxides, alkali metal hydroxides such as sodium hydroxide, alkali metal phenolates such as sodium phenolate, and alkali metal alcoholates, such as sodium methylate, hexahydrotriazines and the like are also useful catalysts.

Mixtures of catalysts are generally beneficial when water is used in the polyurethane-forming formulations. Tertiary amines are effective in catalyzing reaction between water and isocyanate groups. Transition metal salts and complexes are effective in catalyzing polymerization of polyisocyanates and other active hydrogen components, like polyols. Mixtures of such transition metal compounds as compounds of tin, iron and the like with tertiary amine catalysts are, therefore, preferably used in the practice of the invention.

Metal atom-containing catalysts are generally used in a quantity of from about 0.0025 to 0.5 percent by weight based on active hydrogen containing starting components. Amine catalysts are generally used in a quantity of from about 0.001 to 5 percent by weight based on active hydrogen containing starting components. Those skilled in the art are able to select a catalyst composition and quantity suitable to accelerate the reaction between starting components. Representative catalysts and details regarding their use are found in *Kunstoff-Handbuch*, Vol. VII, published by Vieweg and Hochtlen, Carl-Hanser-Verlag, Munich 1966, pp. 96–102.

Active hydrogen compounds suitable for forming the isocyanurate foams are also suitable for forming the polyurethane foams. However, in the case of rigid polyurethane foams, the preferred polyols are polyether polyols, polyester polyols and blends thereof. Among blends containing both polyether and polyester polyols, the blends are preferably those containing polyether polyol having a functionality of from about 3.5 to about 8 inclusive and a crude polyester polyol mixture as described in copending application Ser. No. 282369, filed Dec. 9, 1988 by B. W. Tucker and D. Bhattacharjee, which is incorporated by reference herein in its entirety. The polyether polyols are preferably those initiated by sucrose, glycerine, toluene diamine, aminoethylpiperazine and the like and mixtures thereof. Among such preferred polyether polyols are polyalkylene oxide polymers such as polymers of ethylene oxide, propylene oxide, butylene oxide and the like. The polyols or blends thereof advantageously have equivalent weights of from about 120 to about 230, preferably from about 125 to about 135. Polyols or other active hydrogen compounds are preferably reacted with the polyisocyanate blends containing the treated TDI residues in amounts sufficient to achieve an isocyanate index suitably from about 60 to about 150, preferably from about 90 to about 125, more preferably from about 100 to about 120. The isocyanate index is the ratio of isocyanate groups to active hydrogen groups times 100.

Blowing agents suitable for use in forming polyisocyanurate foams are also suitable for forming polyurethane foams. Preferred blowing agents include carbon dioxide, trichlorofluoromethane, 1,1-dichloro-2,2,2-trifluoro ethane, 1,1-dichloro-1-fluoroethane. The amount of such blowing agent employed is not critical to the invention, but should be sufficient to foam the reaction mixture. Said amount will vary with factors such as the density desired in a foamed product. The density of a rigid polyurethane foam of the invention is advantageously preselected between about 1.90 and 2.27 pounds per cubic foot (pcf), preferably from about 1.90 to about 2.05 pcf. Such densities are advantageously achieved using from about 13 to about 14 percent by weight blowing agent in the absence of any water based on total formulation weight (including all active hydrogen compounds, polyisocyanates and additives). Water is also useful as a blowing agent for use in forming the polyurethane foams. Generally, when water is used, it is present in proportions of from about 0.5 to about 3.5 weight percent of water based on total weight of active hydrogen components. Mixtures of blowing agents are also suitably used.

Advantageously, rigid polyurethane foams of the invention have K factors (mean temperature at 75° F.) of less than about 0.125, preferably less than about 0.120 (BTU in/hr ft² °F.) (less than about 0.0180, less than about 0.0173 W/m K, respectively). The K factor varies somewhat with the active hydrogen compound used. When a polyether polyol is used, the K factor is preferably less than about 0.120, more preferably from about 0.100 to about 0.119 BTU in./hr. ft² °F (less than about 0.0173, from about 0.0144 to about 0.0172 W/m K, respectively). When a polyester polyol or blend comprising predominately polyester polyols is used, the K factor is preferably less than about 0.110, more preferably less than about 0.106 most preferably from about 0.095 to 0.106 (BTU in/hr ft² °F.) (less than about 0.0159, less than about 0.0153, from about 0.0137 to about 0.0153 W/m K, respectively).

Additives such as surface active agents, antistatic agents, plasticizers, fillers, flame retardants, pigments, stabilizers such as antioxidants, fungistatic and bacteriostatic substances and the like are optionally used in foams of the invention. Selection and use of such compounds is within the skill in the art.

In producing foams by the processes of the invention, it is often advantageous use a foam stabilizer, catalyst and blowing agent in balanced proportions to obtain a foam of a preselected cell size, structure and density. Suitable foam stabilizers are generally wetting agents or surface active agents. Nonionic surfactants and wetting agents are generally preferred. Suitable foam stabilizers include hydrophilic, and advantageously water soluble, organosilicon compounds, such as those having a polydimethylsiloxane group attached to a copolymer of ethylene oxide and propylene oxide and the like. Exemplary foam stabilizing compounds are disclosed in U.S. Pat. No. 2,764,565. Such foam stabilizers, surface active compounds and proprietary combinations thereof are generally commercially available with specific instructions as to their use.

The following examples are offered only for purposes of illustrating the process of the invention and are not to be viewed as limiting the present invention. All parts and percentages are on a weight basis unless otherwise indicated. Examples of the invention are designated numerically, with the abbreviation "EX." being used in the tables for examples. Comparative samples are not examples of the invention and are designated with alphabetic characters and are indicated by the abbreviation "C.S." in the tables.

EXAMPLE 1

Treatment of a TDI Residue with an Epoxy Resin at About 180° C.

A sample of toluene diisocyanate (TDI) distillation residue, having a residual toluene diisocyanate content of about 25% by weight, is taken from a thin film evaporator used to purify toluene diisocyanate produced by phosgenation of the corresponding amine. The chloride equivalent of the sample is determined by preparing an admixture of 3.0 grams (g) of the residue and 150 milliliters (mL) of a 3:2 mixture of methanol and 2-methoxy propanol. A solution is formed by heating the admixture on a 235° C. surface for 7.0 minutes, with stirring. About 1 mL of concentrated (85 weight percent) nitric acid is added in the last 2 to 3 minutes of heating. The solution is, then, removed from the heat and allowed to cool for about 2 to 3 minutes. Then the solution is titrated with a dilute (0.0564 Normal (N) solution of silver nitrate to a 280 millivolt (mv) inflection point using silver-silver chloride electrodes. The concentration of hydrolyzable chloride is calculated to be 3819 ppm from the amount of silver nitrate required. Except as otherwise stated, this procedure is followed for the chloride determinations in the subsequent examples and comparative samples.

About 4.7 g of an epoxy resin prepared from bisphenol A and epichlorohydrin having a negligible residual chloride level, a molecular weight of about 362, an equivalent weight of about 176–183 and a viscosity of about 9000 to 105,000 cps, commercially available from The Dow Chemical Company under the trade designation D.E.R. ®383 is added all at once to about 196 g of the residue and mixed therewith to form an admixture. The admixture is heated to 180° C. under a nitrogen blanket with stirring for one hour to produce a treated residue. After that hour, chloride analysis by the procedure used before treatment with the epoxy resin shows a chloride level in the treated residue of about 863 ppm.

The treated residue is allowed to cool overnight. An additional 6.4 g of the epoxy resin is added quickly to the treated residue to form an admixture which is reheated to 180° C. to produce a second treated residue. Heating is maintained for about 15 minutes (min.). After which time, chloride analysis of the second treated residue, as above, showed a chloride content of 270, a reduction of 92% from the initial level.

Comparative Sample A: Epoxy Treatment of a TDI Distillation Residue at Ambient Temperature To analyze a sample of TDI distillation residue, having a chloride content of 4063 ppm as determined by the procedure used in Example 1, for acidity, a mixture of 1.9901 g of the sample with 150 mL of a mixture of 3 parts by volume methanol to 2 parts by volume 2-methoxy propanol is prepared and covered. The mixture is heated on a 235° C. surface with stirring for 7.0 minutes. The mixture is then removed from the heat and stirred until the temperature falls to 50° C. (about 10–15 minutes). Then the mixture is titrated with 0.0157 N methanolic potassium hydroxide and the average acidity of two samples so analyzed is calculated to be 5240 ppm.

Two hundred twenty grams of the TDI residue is mixed with 5.7 g (an amount equivalent to the acidity of the residue) of the epoxy resin used in Example 1 for 24 hours at ambient temperature, approximately 25° C., to produce a very viscous treated residue.

Analysis of chlorides and acidity of the treated residue by the procedures used before treatment showed a chloride content of 2897 (a reduction of 28.7%) and an acidity of 4774 (a reduction of 8.9%).

Comparative Sample B: Treatment With an Aromatic Epoxy Resin at 66° C.

The procedure explained in Example 1 is repeated on a 500 g sample of TDI distillation residues containing 4732 ppm chlorides except that there is a single treatment at 66° C. for 30 minutes then 22 hours at ambient temperature. The treated distillation residue had a chloride content of 3422 ppm.

Comparative Sample C: Use of an Aliphatic Epoxy Compound at Low Temperatures

A sample of 300 g of TDI distillation residue having a chloride content of 2745 ppm, as determined by the procedure of Example 1, is treated by the procedure of Example 2 using 3.16 g (an equivalent amount) of a cycloaliphatic epoxy resin, 2,4-epoxy cyclohexyl methyl-3,4-epoxy cyclohexyl carboxylate, having an equivalent weight of about 227, commercially available from Union Carbide Corp. under the trade designation ERL ®4221, at 66° C. for 30 minutes with stirring. The treated TDI residue is then allowed to stand at ambient temperature, approximately 25° C. for 24 hours. The chloride content is 2062 ppm.

Comparative Sample D: Treatment of TDI Distillation Residue with Epoxidized Soya Bean Oil at 110° and 140°

A 450 g sample of TDI distillation residue having a chloride content of 4478 ppm as determined by the procedure of Example 1 is heated to 110° C. A 50.7 g portion (0.23 equivalents) of epoxidized soya bean oil having an epoxy content of 18%, commercially available from Ferro Corporation under the trade designation Plascheck ®775, is added over a period of 20 minutes with stirring. Concurrently, the sample is heated to 140° C. After that time, a mixture of the treated distillation residue and 500 g of polymeric methylene diphenyllisocyanate (PMDI) having a chloride content of 344 ppm, and a viscosity 44 cps is formed.

Analysis of the mixture shows a chloride content of 1984 ppm, from which the treated residue is calculated to have a chloride content of 3624 ppm. (a 19% reduction).

An additional 61 g of PMDI is blended with the mixture to form a blend having a viscosity of 726 cps.

A Comparison of the chloride reductions achieved in Example 1 and Comparative Samples A–D shows that treatment of TDI distillation residues at 180° C. is more effective than treatment at temperatures of from about 25° to about 110° and 140°.

EXAMPLE 2

Epoxy Treatment of a TDI Residue at Temperatures of From 145°–240°

The procedure of Example 1 is repeated on a 250 g sample of TDI distillation residue having a chloride content of 3396 ppm, except that 13.7 g (3 equivalents relative to the chloride level) of the resin is added over 30 minutes while the temperatures indicated in Table 1 are maintained; 5 to 10 minutes are allowed for digestion before the samples are allowed to cool for 30 minutes; there is no second treatment with epoxy resin. After the 30 minute cooling period, the chloride content is determined by the procedure of Example 1. The percentage loss in hydrolyzable chloride content is recorded in the table.

TABLE 1

| Temperature | % loss of chloride |
| --- | --- |
| 140° C. | −46% |
| 145° C. | −52% |
| 155° C. | −78% |
| 165° C. | −87% |
| 180° C. | −92.5% |
| 210° C. | −93% |
| 240° C. | −85%* |

*At 240° C., insoluble and soluble portions form and are approximately equal in volume. It is only possible to measure the chloride content of the soluble portion. In that portion, the reduction is 85%.

EXAMPLE 3

Larger Scale Epoxy Treatment of TDI Residues and Preparation of Foams Therefrom

The procedure of Example 2 is repeated for three samples of TDI distillation residue as follows:

For Sample 3:1, 905.1 g of TDI distillation residue is maintained at 150° C. while about 10 g of the epoxy resin of Example 1 is added dropwise over 10 minutes. The sample is heated to a temperature of 180° C., and an additional 9.6 g (1 equivalent total) of the resin is added over 15 minutes with stirring. After cooling overnight with stirring, the sample is found to have a chloride content of 608 ppm. The sample is heated to 180° C. and treated with another 2.75 g. of the resin.

For Sample 3:2, 1542 g of TDI distillation residue is heated to 178°–180° C. while about 40.47 g (1.5 equivalents) of the epoxy resin of Example 1 is added dropwise. After the temperature is maintained for an hour, the mixture is allowed to cool to ambient temperature. The next day, the chlorides measured 531 ppm.

For Sample 3:3, 231 g of the epoxy resin is added dropwise over a period of 12 minutes to 1350 g of TDI distillation residue containing 3206 ppm hydrolyzable chloride at a temperature of 150°–170° C. The sample is heated to 180° C. and additional 12 g of resin is added over 15 minutes, for a total of 1.5 equivalents of epoxy compound. The sample is cooled overnight and reheated to 180° C. for the addition of 4.8 additional grams of epoxy resin over 2 minutes, after which the temperature is maintained for 15 minutes before cooling. A total of 1.7 equivalents of epoxy resin is used, and the hydrolyzable chloride concentration is reduced to 615 ppm. This sample is more viscous than Samples 3:1 and 3:2.

Admixtures of the treated TDI distillation residues and polymethylene phenylsiocyanates (PMDI) (having a viscosity of about 44 cps and an isocyanate content of 32%) are prepared having viscosities of 150–200 cps, initially 580 cps rising to 678 after a day, and 1700 cps (Examples 3:1, 3:2, and 3:3, respectively). These admixtures have chloride concentrations of 341, 413 and 396 ppm, respectively; and isocyanate equivalent weights of 136.7, 141.0 and 146., respectively. The hot acidity measurement of sample 3:1 is 82 ppm and that of Sample 3:3 is 181.

Comparative Samples D, E and F are prepared using PMDI samples having viscosities corresponding approximately to the admixtures of Examples 3:1, 3:2, and 3:3, respectively. The PMDI's are PAPI ®27, PAPI ®580, and PAPI ®20, respectively, all commercially available from The Dow Chemical Company. Comparative Sample G is prepared from untreated TDI distillation residue and sufficient PMDI to attain a viscosity of 750 cps.

Foams are prepared from the admixtures and a "B-Side" containing polyol, silicone surfactant, catalysts, blowing agent in the proportions indicated in Table II. The polyol is a polyethylene terephthalate based aromatic polyester polyol commercially available from Freeman Chemical Corp., Chardonol Division under the trade designation Chardol ®625. The silicone is a nonhydrolyzable silicone glycol copolymer commercially available from Dow Corning Corp. under the trade designation Dow Corning 193 Surfactant. Catalyst A is 70 weight percent potassium octoate in diethylene glycol commercially available from Air Products Corp. under the trade designation DABCO K-15, Catalyst B is 2,4,6-tris(dimethyl-aminomethyl) phenol commercially available from Air Products Corp. under the trade designation DABCO TMR-30. The blowing agent is inhibited trichlorofluoromethane, commercially available from E. I. DuPont de Nemours under the trade designation Freon 11B. The "B-Side" is maintained at about 60° F. Mixtures of the amounts of "B-Side" and isocyanate admixture indicated in Table II are combined and stirred with a cutter stir blade stirrer for 10 seconds at 4800 RPM. After stirring the mixtures are immediately poured into 10×10×10 inch cardboard boxes. The following times are observed, each measured from the beginning of mixing:

Cream time: until foaming begins, that is when gas first begins to separate from the liquid
Gel time: when long strings of gelled material can be pulled away form the foam using a tongue depressor inserted in the foam
Tack Free time: foam surface loses its sticky quality
Visual Rise time: when the foam's rising movement is completed
Surface Friability is observed when the foam exhibits a tendency to crumble, flake or become powdery when rubbed or pushed.

The foams are allowed to set overnight and rechecked for surface friability and shrinkage. Friability is Reported in Table II. Examples #:1, #:2 and #:3 and Comparative Samples D and E have slight shrinkage and pull away from the sides of their molds. Comparative Sample F shows no shrinkage, while Comparative Sample shows severe shrinkage. After these properties are checked, the foams are stored for 10–14 days, after which the physical properties indicated in Table II are measured according to the following ASTM methods:

| | |
|---|---|
| Core Density | ASTM D-1622-83 |
| Compressive Strength | ASTM D-1621-73 (1979) |
| K-Factor | ASTM C-177-85 |
| % Closed Cells | ASTM D-2856-87 |
| % Friability (abrasion) | ASTM C-421-77 |

TABLE II

| Sample No. | D★ | 3:1 | E★ | 3:2 | F★ | 3:3 | G★ |
|---|---|---|---|---|---|---|---|
| Isocyanate Viscosity | 200 | 200 | 700 | 700 | 2000 | 2000 | 750 |
| 200 cps PMDI* | 100 | | | | | | |
| 700 cps PMDI* | | | 100 | | | | |
| 2000 cps PMDI* | | | | | 100 | | |
| Untreated TDI residue* | | | | | | | 35 |
| Treated TDI residue* | | 22 | | 35 | | 35 | |
| 44 cps PMDI* | | 78 | | 65 | | 65 | 65 |
| Isocyanate blend † | 54.3 | 55.1 | 54.3 | 55.8 | 55.1 | 56.3 | 56.0 |
| Polyol † | 29.9 | 29.1 | 29.9 | 28.4 | 29.1 | 27.9 | 28.2 |
| Silicone † | 0.75 | 0.75 | 0.75 | 0.75 | 0.75 | 0.75 | 0.75 |
| Catalyst A † | 0.54 | 0.54 | 0.54 | 0.54 | 0.54 | 0.54 | 0.54 |
| Catalyst B † | 0.12 | 0.12 | 0.12 | 0.12 | 0.12 | 0.12 | 0.12 |
| Blowing Agent † | 14.4 | 14.4 | 14.4 | 14.4 | 14.4 | 14.4 | 14.4 |
| Cream (sec) | 21 | 15 | 21 | 15 | 18 | 15 | 30 |
| Gel (sec) | 40 | 27 | 40 | 25 | 32 | 27 | 55 |
| Tack Free (sec) | 52 | 37 | 55 | 28 | 39 | 32 | (1) |
| Visual Rise (sec) | 64 | 50 | 64 | 41 | 51 | 46 | (2) |
| Initial Surface Friability | Yes | Yes | Yes | Yes | Yes | Yes | Yes |
| Surface Friability after 24 Hours | o.k. | Yes | o.k. | o.k. | o.k. | Yes | |
| Density pounds/ft³ (PCF) | 1.74 | 1.89 | 1.93 | 1.92 | 1.95 | 1.86 | (3) |
| Compressive Strength, psi | | | | | | | (3) |
| Y (rise dir) | 30 | 35 | 37 | 36 | 48 | 37 | (3) |
| X (across rise) | 21 | 14 | 12 | 7 | 18 | 15 | (3) |
| Z (across rise) | 8 | 12 | 8 | 6 | 13 | 14 | (3) |
| K Factor (75° F. mean temp), BTU in/hr. ft² °F. | 0.118 | 0.112 | 0.106 | 0.102 | 0.117 | 0.111 | (3) |
| K Factor (75° F. mean temp), W/m K | 0.0170 | 0.0162 | 0.0153 | 0.0147 | 0.0169 | 0.0160 | (3) |
| Closed Cells, % | 98.8 | 97.3 | 97.2 | 97.5 | 98.1 | 96.5 | (3) |
| Friability, % | 29 | 9 | 4.7 | 0.9 | 8 | 3 | (3) |

*amount is expressed as parts per 100 parts by weight isocyanate blend
†amount is expressed as parts per 100 parts by weight total formulation
‡a high viscosity TDI residue is used
★ not an example of this invention
(1) shrinkage is noted after 20 min; after 30 min. foam is still soft with severe shrinkage
(2) foaming incomplete; second pf twp rises normally observed, is not present
(3) properties not measurable since foam is soft and shrunken The data in Table II show that foams having useful properties and having K Factors 0.004 to 0.006 BTU/hr.°F. in. less than foams prepared from PMDI's of equivalent viscosities are prepared from TDI distillation residues treated according to the practice of the invention. Comparative Sample G shows that untreated TDI distillation residues are not similarly useful in these foams.

Comparative Samples H and J

The procedure of Example 3 is repeated using the treated distillation residue of Comparative Sample B for Comparative Sample H and the treated distillation residue of Comparative Sample D for Comparative Sample J.

Before the foam is prepared, 719 g of PMDI having a viscosity of 44 cps is added to the treated distillation residue of Comparative Sample B to form a mixture having a viscosity of 661 cps. The cream time is 8 sec. and initial rise is noted, but there is no secondary rise and no gelling. The foam does not become tack free and collapses into the bottom of the mold.

Comparative Sample D is a blend having a viscosity of 726 cps. A cream time of about 10 sec. and initial rise is noted for foams formed from this mixture, but there is no secondary rise. The foams do not become tack free and eventually shrink into the bottom of the mold.

The unsuccessful attempts to form foams of Comparative Examples H and J show that treatments of TDI distillation residues at temperatures of 140° C. and below do not result in treated residues useable in forming the foams of interest.

EXAMPLES 4–9

Use of Various Epoxy Compounds to Treat TDI Residues

In these examples, different oxiranes are used to treat TDI residues. In each case, TDI residues are collected, analyzed for chloride content, heated to 180° C., and a 3 fold excess (based on chloride) of oxirane is added over a 30–35 minute period during which time the temperature is maintained. After those 30–35 minutes, the treated residue is allowed to sit with stirring at 180° C. for a 5–10 minute digestion period. The mixture is then cooled and analyzed as in Example 1. Example 9, using butylene oxide as oxirane, is carried out in a high pressure reactor to confine the volatile oxide. A pressure of approximately 20–25 psig is reached. The other examples are prepared in glassware under a nitrogen blanket.

TABLE III

| Example | Oxirane | Initial Cl | Final Cl | % reduction |
|---|---|---|---|---|
| 4 | t-Butylphenyl glycidyl ether | 2862 ppm | 235 ppm | 91.7% |
| 5 | Epoxide 8 ($C_{12}$–$C_{14}$ aliphatic, glycidyl ether) | 2774 | 260 | 90.6 |
| 6 | Biphenyl glycidyl ether | 2073 | 329 | 84 |
| 7 | o-Cresyl glycidyl ether | 2720 | 202 | 92.6 |
| 8 | Phenyl glycidyl ether | 3471 | 210 | 93.9 |
| 9 | Butylene Oxide | 4140 | 515 | 87.5 |

The data in Table III show that a variety of monoepoxy compounds are useful in treating TDI distillation residues according to the practice of the invention.

EXAMPLE 10

Preparation of a Rigid Foam Using Epoxy-Treated TDI Residues Without Dilution

A 1482 g sample of TDI residue having 2720 ppm chloride and 35% TDI is placed in a large beaker with a removable glass flange, called a resin kettle, equipped with a high torque stirrer, heating mantle, an infrared heater, and temperature controller. The residue is heated to 180° C. Nitrogen is introduced, and a nitrogen blanket is maintained throughout treatment with 58.8 g of o-cresyl-glycidyl ether, added dropwise over 30–35 minutes. The treated sample is cooled and analyzed. Analysis shows 202 ppm chlorides, 32.6% free TDI, and an isocyanate equivalent weight of 141.3. Viscosity before foaming is 11,200 cps.

A foam is prepared by the procedure of Example 3 using 183.2 g of the treated TDI residue mixed with 28 g of the blowing agent of Example 3. The residue and blowing agent are reacted with a mixture of: 100 g of the polyol Example 3 mixed with 2.5 g of the silicon of Example 3, 1.8 g of Catalyst A, 0.40 g of Catalyst B and an additional 20 g of the blowing agent.

The foam exhibits a cream time of 7 sec., a gel time of 18 sec., a tack free time of 18 sec. and a visual rise time of 21 sec. There is initial surface friability after 3 min or less. After 24 hours, the foam surface is still friable, but the surface friability is gone after 48 hours. Initially the foam is soft to the touch, but hardens within 30 minutes. The cell structure is observed to be very fine.

EXAMPLE 11

Preparation of Polyurethane Foams From Diluted Treated TDI Distillation Residues The procedure of Example 2 is repeated for a 1375 g sample of TDI distillation residue treated with 31.6 g of the epoxy resin of Example 1 at 180° C. for 35 min. The treated residue is mixed with 2507 g of polymethylene phenylisocyanate (PMDI) (having a viscosity of about 44 cps and an isocyanate content of 32%) to produce a blend having a viscosity of 720 cps, an equivalent weight of 143, a hydrolyzable chloride content of 282 ppm and a hot acidity of 125 ppm. The blend is stored at ambient temperatures for about 2 months during which time, the viscosity increases to about 2400–3000 cps.

Foams are prepared from the blend and a "B-Side" containing polyols, silicone surfactant, catalysts, and blowing agent. The polyol is a blend of 101.31 g of a polyethylene terephthalate based aromatic polyester polyol commercially available from Freeman Chemical Corp., Chardonol Division under the trade designation Chardol ® 2513; 50.65 g of a nominally trifunctional aminoethylpiperazine initiated, propylene oxide capped, polyether polyol having an equivalent weight of 121.86 and 50.65 g of a sucrose initialed propylen oxie capped polyether polyol having an equivalent weight of 107.25 commercially available from Texaco Corp. under the trade designation Thanol ® R-575. The silicone is 3.65 g (1.8 parts per hundred parts polyol) of a polydimethylsiloxane-polyoxyalkylene block copolymers surfactant commercially available from Goldschmidt Corp. under the trade designation B-8416. The catalyst is 0.81 g (0.4 parts per hundred parts polyol) of N,N'-dimethylcyclohexylamine commercially available from Air Products Corp. under the trade designation Polycat ® 8. The blowing agent is 68.1 g (14 weight percent based on total formulation) inhibited trichlorofluoromethane, commercially available from E. I. DuPont de Nemours under the trade designation Freon 11B. The "B-Side" is stirred very well and maintained with the designated level of blowing agent.

Samples of the "B-Side" mixture and sufficient isocyanate to produce an isocyanate index (ratio of isocyanate groups to active hydrogen groups) of 1.05 are combined and stirred very vigorously with a drill press for 10 seconds. After stirring, the mixtures are immediately poured into 14×14×4 inch aluminum molds heated at 115°–120° F. The foam is maintained at that temperature for 10 minutes then removed from the mold while hot. After 24 hours, a 12×12×1 inch core sample is cut for determination of K-factor by the procedure of ASTM C-518-85. The density is determined by the procedure of ASTM D-1622-83. The K-factor (75° F. mean temp) in. is 0.106 BTU in./ft². hr. °F. and the density is 1.90 pcf.

Comparative Sample K: A Foam Similar to That of Example 11, but Using PMDI as the Isocyanate The procedure of Example 11 is repeated using as the isocyanate, a polymethylene phenylisocyanate (PMDI) (having a viscosity of about 200 cps commercially available from the The Dow Chemical Company under the trade designation PAPI® 27. The K-factor (75° F. mean temp) is 0.105 BTU in./ft². hr. °F. and the density is 2.05 pcf.

EXAMPLES 12-18 AND COMPARATIVE SAMPLES L-S

Preparation of Polyurethane Foams

The procedure of Example 11 is repeated using as the polyol and blowing agents in the "B-side" mixture, the following:

(A): For Examples 12-14 and Comparative Samples L-N: The polyol is a mixture of 50 parts by weight of nominally trifunctional, amino piperazine initiated propylene oxide capped polyether polyol having an equivalent weight of 121.86 and 25 parts by weight of each of (a) a sucrose/glycerine initiated, propylene epoxide capped polyether polyol having a nominal functionality of about 6.9, having a viscosity of 23,000 cps having an equivalent weight of 152 commercially available form The Dow Chemical Company under the trade designation Voranol® 370 and (b) sucrose/glycerine initiated, propylene oxide capped, polyether polyol having a nominal functionality of about 4 and a viscosity of 5,500 cps commercially available from The Dow Chemical Company under the trade designation Voranol® 490. No water is used in the "B-side" mixture for Example 12 and Comparative Sample L wherein 14 weight percent blowing agent is used; while 0.5 parts of water and 12.2 weight percent blowing agent are used in Example 13 and Comparative Sample M; 1 part water and 10.3 weight percent blowing agent are used in Example 14 and Comparative Sample N.

(B) For Examples 15-17 and Comparative Samples P-R: The polyol is a blend of 77 parts Voranol 370, 13 parts methyldiethanolamine and 14 parts Voranol 2110 (a nominally difunctional, propylene oxide capped polyethylene polyol having an equivalent weight of 510, commercially available from The Dow Chemical Company. No water is used in the "B-side" mixture for Example 15 and Comparative Sample P wherein 14 weight percent blowing agent is used; while 0.5 parts of water and 12.2 weight percent blowing agent are used in Example 16 and Comparative Sample Q; 1 part water and 10.3 weight percent blowing agent are used in Example 17 and Comparative Sample R.

The K-Factors and densities are measured as in Example 11 and recorded in Table IV.

TABLE IV

| sample or example number | Water | K-factor (75° F. mean temp) in BTU in. /ft². hr. °F. | K-factor (75° F. mean temp) in W/m K | Density in pcf |
|---|---|---|---|---|
| 11 | 0 | 0.106 | 0.0153 | 1.90 |
| K* | 0 | 0.105 | 0.0152 | 2.05 |
| 12 | 0 | 0.108 | 0.0156 | 2.04 |
| L* | 0 | 0.109 | 0.0157 | 2.08 |
| 13 | 0.5 | 0.109 | 0.0157 | 2.05 |
| M* | 0.5 | 0.111 | 0.0160 | 2.09 |
| 14 | 1.0 | 0.115 | 0.0166 | 2.08 |
| N* | 1.0 | 0.116 | 0.0167 | 1.97 |

TABLE IV-continued

| sample or example number | Water | K-factor (75° F. mean temp) in BTU in. /ft². hr. °F. | K-factor (75° F. mean temp) in W/m K | Density in pcf |
|---|---|---|---|---|
| 15 | 0 | 0.119 | 0.0172 | 2.27 |
| P* | 0 | 0.116 | 0.0167 | 1.98 |
| 16 | 0.5 | 0.114 | 0.0164 | 2.22 |
| Q* | 0.5 | 0.120 | 0.0173 | 2.09 |
| 17 | 1.0 | 0.117 | 0.0169 | 2.20 |
| R* | 1.0 | 0.119 | 0.0172 | 2.06 |

*NOT AN EXAMPLE OF THE INVENTION

The data in Table IV shows that treated TDI distillation residues are useful in preparing foams having useful K-factors used in formulations in solving both polyether polyols and blends of polyester polyols with polyether polyols.

EXAMPLES 18-27

Preparation of Polyurethane Foams Using More Dilute Blends of Treated TDI Distillation Residues The blend of treated TDI distillation residue with PMDI of Example 11 is further diluted with the same PMDI in the following weight ratios (of blend to PMDI) to produce blends having the indicated isocyanate equivalents and viscosities:

| Blend | Ratio | Isocyanate Equivalent | Viscosity at 23° C. |
|---|---|---|---|
| Blend A | 1:2 | 136.3 | 200 cps |
| Blend B | 1:1 | 137.5 | 310 cps |
| Blend C | 2:1 | 139.0 | 460 cps |

Foams are prepared by the procedure of Example 11 using the polyols or mixtures thereof indicated in Table V. K-Factor and density are measured as in Example 11 and reported in Table V.

TABLE V

| sample or example number | Blend | Polyol of Example | water | K-factor (75° F. mean temp) in BUT/ hr. °F. | K-factor (72° F. mean temp) in W/m K | Density in pcf |
|---|---|---|---|---|---|---|
| 18 | A | 11 | 0 | 0.103 | 0.0149 | 1.92 |
| 19 | B | 11 | 0 | 0.099 | 0.0143 | 1.97 |
| 20 | C | 11 | 0 | 0.103 | 0.0149 | 1.94 |
| 21 | B | 12 | 0 | 0.106 | 0.0153 | 2.14 |
| 22 | C | 12 | 0 | 0.112 | 0.0162 | 2.10 |
| 23 | A | 13 | 0 | 0.107 | 0.0154 | 2.10 |
| 24 | B | 13 | 0 | 0.105 | 0.0152 | 1.97 |
| 25 | C | 13 | 0 | 0.105 | 0.0152 | 2.04 |
| 26 | A | 13 | 0.5 | 0.112 | 0.0162 | 2.03 |
| 27 | A | 13 | 1.0 | 0.119 | 0.0172 | 1.94 |

The data in Table V shows that treated TDI distillation residue is useful when reacted with a variety of polyols and in a variety of mixtures with polymethylene polyphenylisocyanate to produce polyurethane foams having useful K-factors.

We claim:

1. A method of treating toluene diisocyanate distillation residues comprising reacting the residues with at least about 0.5 equivalents, based on hydrolyzable chloride concentration in the residues, of an epoxy compound at a temperature of from about 155° C. to about 220° C. to produce a treated distillaton residue having a hydrolyzable chloride concentration of less than about 800 parts per million (ppm).

2. The method of claim 1 wherein the temperature is from about 165° C. to about 180° C.

3. The method of claim 1 wherein from about 0.5 to about 20 equivalents of the epoxy compound is used.

4. The method of claim 3 wherein from about 0.75 to about 3 equivalents of the epoxy compound is used.

5. The method of claim 4 wherein the epoxy compound is a monoepoxy compound.

6. The method of claim 5 wherein the epoxy compound is an alkylene oxide or a glycidyl ether.

7. The method of claim 4 wherein the epoxy compound is an epoxy resin compound.

8. A treated toluene diisocyanate distillation residue which is the product of reacting the residue with an epoxy compound at a temperature of from about 155° C. to about 220° C., said treated toluene diisocyanate distillation residues having a hydrolyzable chloride concentration of less than about 800 parts per million (ppm).

9. The treated toluene diisocyanate distillation residue of claim 8 wherein the chloride concentration is less than about 600 ppm.

10. The treated toluene diisocyanate distillation residue of claim 9 wherein the chloride concentration is less than about 400 ppm.

11. The treated toluene diisocyanate distillation residue of claim 10 wherein the chloride concentration is less than about 300 ppm.

12. A polymer prepared by reacting a reaction mixture containing components:
(a) an active hydrogen compound or mixture thereof; and
(b) a polyisocyanate component containing
   (1) from about 1 to about 100 weight percent based on total weight of polyisocyanate component (b) of a treated toluene diisocyanate distillation residue which is the product of reacting the residue with an epoxy compound at a temperature of from about 155° C. to about 220° C., said treated toluene diisocyanate distillation residue having a hydrolyzable chloride level of less than about 800 parts per million (ppm).

13. The polymer of claim 12 wherein the reaction mixture additionally contains from 0 to about 99 weight percent based on total weight of polyisocyanate component (b) of a different polyisocyanate.

14. A rigid isocyanurate foam formed of the polymer of claim 13.

15. The foam of claim 14 wherein the reaction mixture additionally contains, as component (c), at least one blowing agent.

16. The foam of claim 15 wherein the reaction mixture additionally contains, as component (d), at least one trimerization catalyst.

17. The foam of claim 16 wherein the treated toluene diisocyanate distillation residue is from about 15 to about 75 weight percent of polyisocyanate component (b).

18. The foam of claim 17 wherein the treated toluene diisocyanate distillation residue is from about 20 to about 40 weight percent of polyisocyanate component (b).

19. The foam of claim 18 wherein the treated toluene diisocyanate distillation residue is from about 90 to about 100 weight percent of polyisocyanate component (b).

20. The foam of claim 17 having a K Factor, as determined by ASTM C 177-85 or ASTM C 518-85, at least about 3% lower than that of a foam having the same components (a) and (c), but having as a polyisocyanate component, a polymeric methylene diphenylisocyanate having a viscosity about equal to that of polyisocyanate component (b).

21. The foam of claim 20 having a K Factor at least about 0.003 BTU in./hr. ft$^2$ °F. ($4.3 \times 10^{-4}$ w/m K) lower than that of a foam having the same (a) and (c), but having as a polyisocyanate component, a polymeric methylene diphenylisocyanate having a viscosity about equal to that of polyisocyanate component (b).

22. The foam of claim 17 having a K Factor of less than about 0.115 BTU in/hr. ft$^2$ °F. (less than about 0.0166 w/m K).

23. The foam of claim 22 having a K Factor of from about 0.102 to about 0.112 BTU in/hr ft$^2$ °F. (from about 0.0147 to about 0.0161 w/m K).

24. The foam of claim 17 wherein the polyisocyanate component (b) has a hydrolyzable chloride content of less than about 400 ppm.

25. The foam of claim 24 wherein the polyisocyanate component (b) has a hydrolyzable chloride content of less than about 300 ppm.

26. The foam of claim 17 wherein the polyisocyanate component (b) has a viscosity of less than about 10,000 centipoise.

27. The foam of claim 26 wherein the polyisocyanate component (b) has a viscosity of from about 30 to about 3,000 centipoise.

28. The foam of claim 27 wherein the polyisocyanate component (b) has a viscosity of from about 40 to about 2,500 centipoise.

29. The foam of claim 17 having a friability, as determined by ASTM C 421-85, less than about 60% of that of a foam having the same (a) and (c), but having as a polyisocyanate component, a polymeric methylene diphenylisocyanate having a viscosity about equal to that of polyisocyanate component (b).

30. The foam of claim 19 having a friability, as determined by ASTM C 421-85, less than about 50% of that of a foam having the same (a) and (c), but having as a polyisocyanate component, a polymeric methylene diphenylisocyanate having a viscosity about equal to that of polyisocyanate component (b).

31. The foam of claim 22 having a friability, as determined by ASTM C 421-85, less than about 40% of that of a foam having the same (a) and (b), but having as a polyisocyanate component, a polymeric methylene diphenylisocyanate having a viscosity about equal to that of polyisocyanate component (c).

32. A rigid polyurethane foam formed of the polymer of claim 13.

33. The foam of claim 32 wherein the reaction mixture additionally contains, as component (c), at least one blowing agent.

34. The foam of claim 33 wherein the reaction mixture additionally contains, as component (d), at least one polyurethane catalyst.

35. The foam of claim 34 wherein the treated toluene diisocyanate distillation residue is at least about 10 weight percent of polyisocyanate component (b).

36. The foam of claim 35 wherein the treated toluene diisocyanate distillation residue is at least about 25 weight percent of polyisocyanate component (b).

37. The foam of claim 20 having a K Factor as determined by the procedures of ASTM C 518-85 or ASTM C 177-85 of less than about 0.125 BTU in./hour °F. ft.² (0.0180 W/m K).

38. The foam of claim 37 having a K Factor of less than about 0.120 BTU in./hour °F. ft.² (0.0173 W/m K).

39. The foam of claim 38 wherein at least about 85 weight percent of component (a) is a polyether polyol or a mixture of polyether polyols and the K factor is from about 0.100 to about 0.119 BTU in./hour °F. ft² (0.0144 to about 0.0172 W/m K).

40. The foam of claim 38 wherein component (a) is a mixture of (i) at least one polyether polyol having a nominal functionality of from about 3.5 to about 8 inclusive and (ii) at least one polyester polyol, wherein the K factor is from about 0.095 to about 0.106 BTU in./hour °F. ft.² (0.0137 to about 0.0153 W/m K).

41. The foam of claim 35 wherein the polyisocyanate component (b) has a hydrolyzable chloride content of less than about 400 ppm.

42. The foam of claim 17 wherein the polyisocyanate component (b) has a viscosity of less than about 1,000 centipoise.

43. A process for preparing a polymer by reacting a reaction mixture containing components:
   (a) an active hydrogen compound or mixture thereof; and
   (b) a polyisocyanate component containing
      (1) from about 1 to about 100 weight percent based on total weight of polyisocyanate component (b) of a treated toluene diisocyanate distillation residue which is the product of reacting the residue with an epoxy compound at a temperature of from about 155° C. to about 220° C., said treated toluene diisocyanate distillation residue having a hydrolyzable chloride level of less than about 800 parts per million (ppm).

44. The process of claim 43 wherein the polymer is in the form of a foam.

45. The process of claim 44 wherein the foam is a polyisocyanurate foam.

46. The process of claim 44 wherein the foam is a polyurethane foam.

* * * * *